(12) United States Patent
Kawashiro et al.

(10) Patent No.: US 8,007,480 B2
(45) Date of Patent: Aug. 30, 2011

(54) DELIVERY DEVICE, DELIVERY CONTAINER, AND EYE DROPPER PROVIDED WITH THE SAME

(75) Inventors: Yasushi Kawashiro, Anan (JP); Yuji Sugahara, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1013 days.

(21) Appl. No.: 10/570,271

(22) PCT Filed: Aug. 30, 2004

(86) PCT No.: PCT/JP2004/012864
§ 371 (c)(1),
(2), (4) Date: Dec. 13, 2006

(87) PCT Pub. No.: WO2005/023665
PCT Pub. Date: Mar. 17, 2005

(65) Prior Publication Data
US 2007/0093765 A1   Apr. 26, 2007

(30) Foreign Application Priority Data

Sep. 2, 2003  (JP) ................................. 2003-310441

(51) Int. Cl.
*A61M 35/00* (2006.01)
(52) U.S. Cl. .................. 604/289; 604/294; 604/295
(58) Field of Classification Search .................. 604/289, 604/294–295
See application file for complete search history.

(56) References Cited

U.S. PATENT DOCUMENTS
4,722,449 A    2/1988  Dubach
(Continued)

FOREIGN PATENT DOCUMENTS
EP    0 538 162 A1    4/1993
(Continued)

OTHER PUBLICATIONS
International Preliminary Report on Patentability, dated Jun. 20, 2006.
(Continued)

*Primary Examiner* — Michele Kidwell
(74) *Attorney, Agent, or Firm* — Finnegan, Henderson, Farabow, Garrett & Dunner, L.L.P.

(57) ABSTRACT

The present invention has an object to provide a delivery device that is capable of preventing a content liquid from flowing back and achieving aseptic delivery of liquid drop (dripping), and provide a delivery container, and an eye dropper that can eliminate or reduce the use of an antiseptic agent and achieve smooth delivery of the liquid. The delivery device 10 of the present invention comprises the outlet portion 11 of a substantially bottomed tubular shape having the outlet orifice 12, the valve element support portion 13 of substantially cylindrical shape that is secured in the outlet portion 11 with a distal end 13a thereof exposed through the outlet orifice 12 to the outside of the outlet portion 11, and a valve element 14 that is secured in the outlet portion 11 with a distal end 14a thereof exposed through the outlet orifice 12 to the outside of the outlet portion 11. The distal end 14a of the valve element makes contact with the valve element support portion 13 so as to close the outlet orifice 12 when there is no liquid pressure applied to the distal end portion from the upstream U, and deforms so as to form a flow passage between the distal end portion and the valve element support portion 13 when subjected to liquid pressure applied from the upstream U. The delivery container 30 of the present invention has the delivery device 10 installed at the mouth 31a of the squeeze bottle 31.

2 Claims, 18 Drawing Sheets

U.S. PATENT DOCUMENTS

| | | | |
|---|---|---|---|
| 5,271,513 A | 12/1993 | Crosnier et al. | |
| 5,339,972 A | 8/1994 | Crosnier et al. | |
| 6,923,345 B1 * | 8/2005 | Laible | 222/185.1 |
| 2002/0153386 A1 | 10/2002 | Uetake et al. | |
| 2002/0190079 A1 * | 12/2002 | Hamamoto | 222/105 |
| 2003/0085240 A1 | 5/2003 | Dark | |

FOREIGN PATENT DOCUMENTS

| | | |
|---|---|---|
| FR | 747465 B | 6/1933 |
| JP | 60-90151 | 5/1985 |
| JP | 62-52047 | 3/1987 |
| JP | 2001-179017 | 7/2001 |
| JP | 2001-206454 | 7/2001 |
| JP | 2002-2755 | 1/2002 |
| JP | 2002-053629 | 2/2002 |
| JP | 2002-053762 | 2/2002 |
| JP | 2002-80055 | 3/2002 |
| JP | 2003-063576 | 3/2003 |
| WO | WO 00/06460 | 2/2000 |

OTHER PUBLICATIONS

Office Action dated Jul. 1, 2010 corresponding Japanese Patent Application No. 2005-513687.

* cited by examiner

PRIOR ART

PRIOR ART

DELIVERY DEVICE, DELIVERY CONTAINER, AND EYE DROPPER PROVIDED WITH THE SAME

TECHNICAL FIELD

The present invention relates to a delivery device that has backflow preventing effect for aseptically delivering a liquid contained in a squeeze bottle, and to a delivery container and an eye dropper that have the delivery device installed at the mouth thereof and is capable of aseptically delivering the content liquid.

BACKGROUND ART

A container used to drip a liquid contained therein such as an eye dropper employs a liquid delivery device 90 installed at a mouth 92a of a container body 92 such as one shown in FIG. 13(a), (b). The delivery device 90 discharges the content liquid in the form of drop 94 through an outlet orifice 91 when the container body 92 is depressed.

With respect to the delivery device 90 shown in FIG. 13, however, since outside air is taken in through an outlet opening 93 so as to restore the container body 92, that has been deformed by depressing, into the original shape after discharging the liquid, there has been such a problem that microorganisms such as bacteria and dust deposited on the outlet opening 93 enter the container body 92 when the liquid (ophthalmic solution, for example) 95 that has remained in the outlet opening 93 flows back into the container body 92 (refer to FIG. 14(a), (b)). In case the container is an eye dropper, in particular, it is very likely that such a problem occurs as the outlet opening 93 can easily catch microorganisms and dust through contact with cornea and/or eye lid.

Since the entry of microorganisms and dust into the container body may cause the liquid contained therein to decay or deteriorate, the liquid (ophthalmic solution) contained in the eye dropper contains an antiseptic agent such as benzalkonium chloride or parabens (paraoxybenzoate esters) mixed therein. However, there remain such problems that it is difficult to prescribe a proper composition containing an antiseptic agent depending on the type and purpose of the liquid contained in the container, and that the antiseptic agent added to the ophthalmic solution may cause a side effect such as allergy in the user.

For these reasons, it has been studied to eliminate or reduce the use of antiseptic agents. For example, disposable eye droppers comprising small container that contains a very small quantity of ophthalmic solution and is sealed without antiseptic agent added thereto have been provided. However, disposable eye droppers have been restricted to particular applications and are not used for general purpose due to the disadvantage in terms of cost.

Patent Document 1(Japanese Unexamined Patent Publication No. 2002-80055) discloses a delivery container provided with a filter that employs a so-called delamination bottle having an outer layer (outer container) and an inner layer (inner container) which is provided delaminatably on the inside of the outer layer. Since this delivery container prevents outside air from flowing into the container through the outlet opening after delivering the content liquid, contamination of the liquid in the container by bacteria, dust and the like can be prevented. However, this container has a problem of high manufacturing cost since it is necessary to provide an inner container that is easily deformed according to a change in the inside pressure of the container caused by the delivery of the liquid.

Patent Document 2(Japanese Unexamined Patent Publication No. 2001-179017) and Patent Document 3 (Japanese Unexamined Patent Publication No. 2001-206454) disclose antibacterial containers having a porous filter that has pores small enough to prohibit the passage of bacteria and dust and is disposed at the outlet opening thereof. In this case, however, when the porous filter dries up after being wetted by a liquid medicine or the like, there is a possibility that the filter is choked with the solute contained in the liquid. When the content of the container is a suspension, the problem of choked filter is more likely to occur. Moreover, while the containers described in Patent Documents 2 and 3 employ the porous filters made of sintered metal or sintered resin, in which case fine particles of the sintered material may be mixed in the liquid so as to be delivered therewith out of the container.

Thus there have been demands for a delivery container such as eye dropper that can prevent the content liquid (liquid medicine) from flowing back through the outlet orifice, and achieve aseptic delivery (dripping) of the content liquid.

DISCLOSURE OF THE INVENTION

An object of the present invention is to provide a delivery device that is capable of preventing a content liquid from flowing back and achieving aseptic delivery of liquid drop (dripping), and provide a delivery container and an eye dropper that can eliminate or reduce the use of an antiseptic agent which is added for the purpose of preventing the content liquid from being decayed or deteriorated, and achieve smooth delivery of the liquid without choking even when the content liquid is a suspension.

A first delivery device of the present invention that achieves the object described above comprises an outlet portion of a substantially bottomed tubular shape or a substantially bowl like shape having an outlet orifice disposed at the bottom thereof, a valve element support portion of a substantially cylindrical shape that is secured in the outlet portion with a distal end thereof being exposed through the outlet orifice to the outside of the outlet portion, and a valve element made of an elastic material that is secured in the outlet portion with the distal end thereof being exposed through the outlet orifice to the outside of the outlet portion, wherein the distal end portion of the valve element makes contact with the valve element support portion so as to close the outlet orifice when there is no liquid pressure applied to the distal end portion from the upstream, the outlet orifice side being defined as the downstream, and deforms so as to form a flow passage between the distal end portion and the valve element support portion when subjected to liquid pressure applied from the upstream.

A second delivery device of the present invention that achieves the object described above comprises an outlet portion of a substantially bottomed tubular shape or a substantially bowl like shape having an outlet orifice at the bottom thereof, a valve element support portion of a substantially disk shape that is secured in the outlet portion in the vicinity of the outlet orifice, and a valve element made of an elastic material that is secured in the outlet portion with a distal end thereof being exposed through the outlet orifice to the outside of the outlet portion, wherein the distal end portion of the valve element makes contact with the valve element support portion so as to close the outlet orifice when there is no liquid pressure applied to the distal end portion from the upstream, the outlet orifice side being defined as the downstream, and deforms so as to form a flow passage between the distal end portion and the valve element support portion when subjected to liquid pressure applied from the upstream.

In the first and second delivery devices of the present invention, the valve element that controls closing and opening of the outlet orifice is made of an elastic material. When there is no liquid pressure exerted thereon applied from the upstream, the valve element makes contact with the valve element support portion and closes the outlet orifice. When subjected to liquid pressure applied from the upstream, the valve element deforms so as to form a clearance (flow passage) between itself and the valve element support portion, and open the outlet orifice. When the outlet orifice is opened, the outlet orifice and the upstream side (a squeeze bottle or the like connected to the delivery device) of the outlet portion become connected to communicate with each other, thereby achieving the delivery (dripping) of liquid from the outlet orifice.

To achieve delivery of a liquid medicine or the like from the outlet orifice of the first or second delivery device according to the present invention, a pressure may be applied to the squeeze bottle that is connected to the delivery device. As the pressure is applied, the valve element receives the pressure of the liquid (liquid medicine or the like) contained in the squeeze bottle applied from the upstream, so that the valve element deforms and opens the outlet orifice. When the pressure on the squeeze bottle is removed, the deformed squeeze bottle has a drive to restore the initial shape and draw in the outside air. However, since the squeeze bottle is a container that is squeezed to deliver the content thereof similarly to a tooth paste tube, it has intrinsically small negative pressure that acts on the outlet orifice as the bottle is going to restore the initial shape. In addition, since the delivery device of the present invention has such a structure as the valve element deforms when subjected to the liquid pressure applied from the upstream thereby to form a clearance (flow passage) between itself and the valve element support portion, the negative pressure generated as the bottle restores the initial shape has an effect of accelerating the restoration of the initial shape of the deformed valve element. As a result, when the pressure on the squeeze bottle (and the accompanying negative pressure of the liquid applied to the valve element) is removed, the clearance (flow passage) that was formed in the outlet orifice by the deformation of the valve element is immediately blocked, so that the valve element functions as a check valve in the delivery device of the present invention.

Thus the first and second delivery devices of the present invention can prevent the liquid that has been discharged through the outlet orifice from flowing back and prevent foreign matter such as bacteria and dust from entering the container along with the liquid. Such delivery device is preferably applied to the outlet portion of an eye dropper, for example, that employs a squeeze bottle.

The delivery device according to the present invention can also be used as the outlet portion of a so-called delamination bottle that has an outer layer (outer container) and an inner layer (inner container) which is provided delaminatably on the inside of the outer layer. In this case, too, the delivery device can prevent the liquid that has been discharged through the outlet orifice from flowing back and prevent foreign matter such as bacteria and dust from entering the container with the liquid.

The delivery container of the present invention that achieves the aforementioned object has the first or second delivery device installed at the mouth of a squeeze bottle.

A first delivery container of the present invention has a delivery device that is installed at the mouth of a squeeze bottle and comprises an outlet portion of a substantially bottomed tubular shape or a substantially bowl like shape having an outlet orifice disposed at the bottom thereof, a valve element support portion of substantially cylindrical shape that is secured in the outlet portion with a distal end thereof being exposed through the outlet orifice to the outside of the outlet portion, and a valve element made of an elastic material that is secured in the outlet portion with the distal end thereof being exposed through the outlet orifice to the outside of the outlet portion, wherein the distal end portion of the valve element makes contact with the valve element support portion so as to close the outlet orifice when there is no liquid pressure applied to the distal end portion from the squeeze bottle side, and deforms so as to form a flow passage between the distal end portion and the valve element support portion when subjected to liquid pressure applied from the squeeze bottle side.

A second delivery container of the present invention has a delivery device that is installed at the mouth of a squeeze bottle and comprises an outlet portion of a substantially bottomed tubular shape or a substantially bowl like shape having an outlet orifice disposed at the bottom thereof, a valve element support portion of a substantially disk shape that is secured in the outlet portion in the vicinity of the outlet orifice, and a valve element made of an elastic material that is secured in the outlet portion with a distal end thereof being exposed through the outlet orifice to the outside of the outlet portion, wherein the distal end portion of the valve element makes contact with the valve element support portion so as to close the outlet orifice when there is no liquid pressure applied to the distal end portion from the squeeze bottle side, and deforms so as to form a flow passage between the distal end portion and the valve element support portion when subjected to liquid pressure applied from the squeeze bottle side.

In the first and second delivery containers of the present invention, the delivery device installed at the mouth of the squeeze bottle is the first or second delivery device according to the present invention that, when a pressure is applied to the squeeze bottle, can deliver (dripping) the content liquid through the outlet orifice by deforming the valve element as mentioned above. When the pressure on the squeeze bottle is removed so as to remove the liquid pressure on the valve element, the outlet orifice is immediately closed, so that the valve element functions as a check valve. Thus the first and second delivery containers of the present invention have high capability to prevent the liquid that has been discharged from flowing back into the squeeze bottle and to prevent foreign matter such as bacteria and dust from entering the squeeze bottle with the liquid. As a result, it is made possible to eliminate or reduce the use of chemicals (for example, antiseptic agent) added for the purpose of preventing the content liquid from being decayed or deteriorated. Moreover, since the delivery container of the present invention does not use a porous filter in the outlet portion, choking of the outlet orifice does not occur. Thus smooth delivery of the liquid can be achieved even when the content liquid is a suspension.

Both the first and second delivery containers of the present invention may have such a constitution as:
(I) The squeeze bottle has a thin film that seals the mouth thereof, and the outlet portion has a hollow puncture needle disposed therein having a pointed end directed toward the squeeze bottle side, so that the puncture needle pierces the thin film when the outlet portion is screwed or fitted onto the squeeze bottle; or
(II) The outlet portion has a plug disposed therein that makes contact with an inner surface of the squeeze bottle and blocks between the outlet portion and the squeeze bottle, so that a flow passage is formed between the plug and the inner surface of the squeeze bottle when the outlet portion is screwed or fitted onto the squeeze bottle, or screw engagement or fitting of the outlet portion and the squeeze bottle is loosened.

When the squeeze bottle is provided with the thin film described in (I), the content liquid of the squeeze bottle can be kept hermetically preserved before the delivery container is used, and therefore aseptic condition can be ensured. When the outlet portion is provided with the plug described in (II), not only aseptic condition of the content liquid can be ensured before the delivery container is used, but also the content liquid can be kept hermetically preserved again if the use of the delivery container is interrupted, in which case the flow passage between the plug and the inner surface of the squeeze bottle is closed.

Both the first and second delivery containers of the present invention can be preferably used as an eye dropper containing an ophthalmic solution.

BEST MODE FOR CARRYING OUT THE INVENTION

Now embodiments of the delivery device and the delivery container and the eye dropper that have the delivery device according to the present invention will be described in detail with reference to the accompanying drawings.

Figure 1:
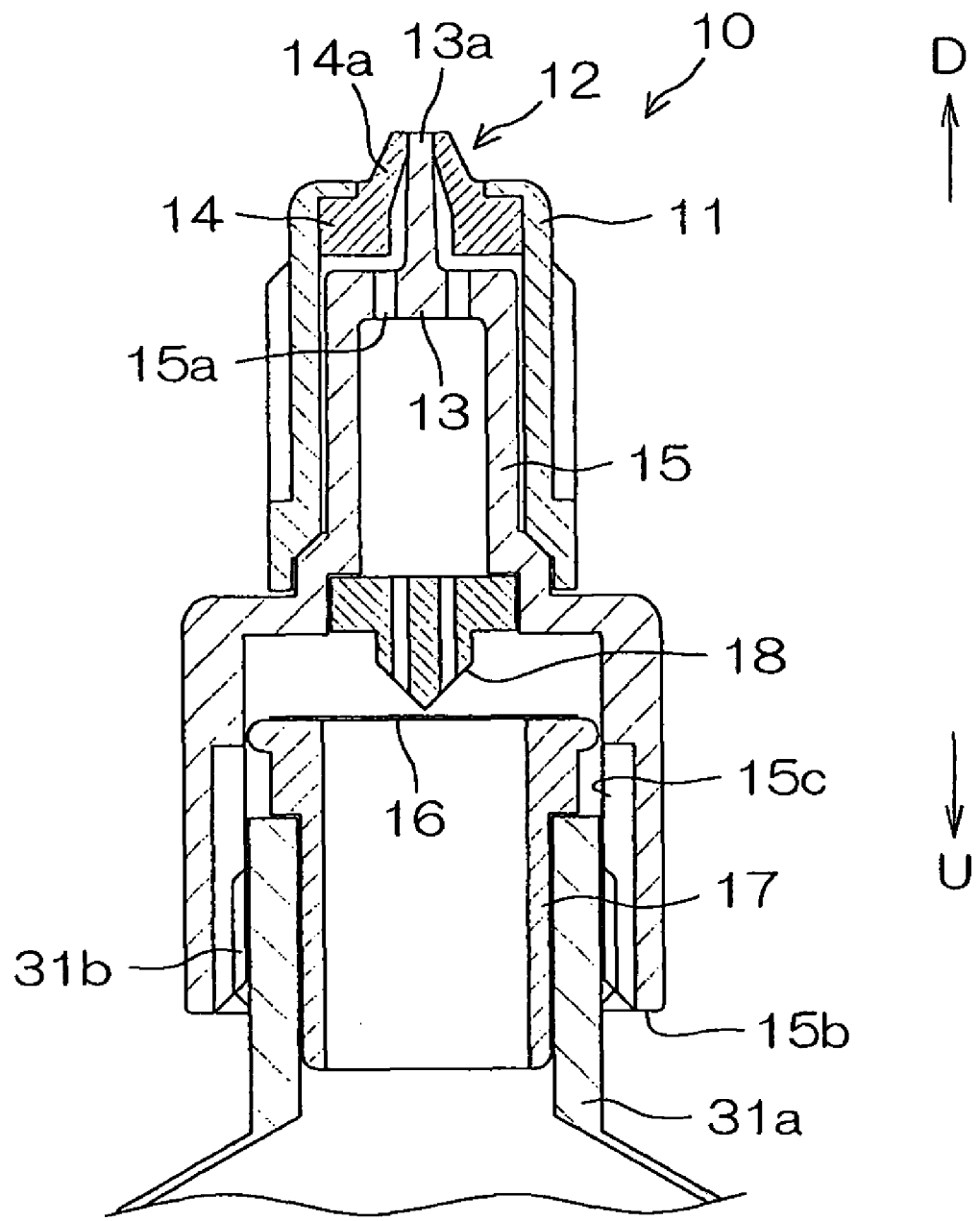
FIG. 1 is a sectional view showing an embodiment of the first delivery device of the present invention.

The delivery device 10 shown in FIG. 1 is an embodiment of the first delivery device of the present invention, and comprises an outlet portion 11 of a substantially bottomed tubular shape, a valve element support portion 13 of substantially cylindrical shape that is secured in the outlet portion 11 with the distal end 13*a* thereof being exposed through the outlet orifice 12 to the outside of the outlet portion 11, and a valve element 14 that is secured on the inner surface of the outlet portion 11 in the vicinity of the outlet orifice 12 with the distal end 14*a* thereof being exposed through the outlet orifice 12 to the outside of the outlet portion 11.

The valve element support portion 13 is connected to a tube 15, and is secured by welding the tube 15 onto the inner surface of the outlet portion 11 so that the distal end 13*a* of the valve element support portion is exposed at the outlet orifice 12 to the outside of the outlet portion 11. The tube 15 has a hole 15*a* that makes a flow passage for the content liquid to flow from within the tube 15 to the outlet orifice 12. The tube 15 is connected to the threaded portion 31*b* provided on the mouth 31*a* of the squeeze bottle 31 by screwing a threaded portion 15*c* provided on the inner circumference of the opening end 15*b*.

The valve element 14, when subjected to liquid pressure applied from the upstream U, bends toward the outside of the outlet portion 11 (the side of outer circumference of the valve element 14 at the distal end 14*a*) so as to form a flow passage between itself and the valve element support portion 13. The valve element 14 and the outlet portion 11 can be molded integrally by using a thermoplastic elastomer as the material to form the former and a thermoplastic resin as the material to form the latter. The valve element made of a thermoplastic elastomer is sticky in nature and is capable of easily blocking. Therefore, while it is difficult to mold the valve element and the outlet portion separately, manufacturing process can be made easier by molding the valve element 14 and the outlet portion 11 integrally, thereby improving the productivity. Method for molding the valve element and the outlet portion integrally may be, for example, multicolor molding or insertion molding.

The tube 15 has a hollow puncture needle (hollow needle) 18 disposed therein with a pointed end of the hollow needle 18 directed toward the squeeze bottle side (upstream U).

Figure 2:
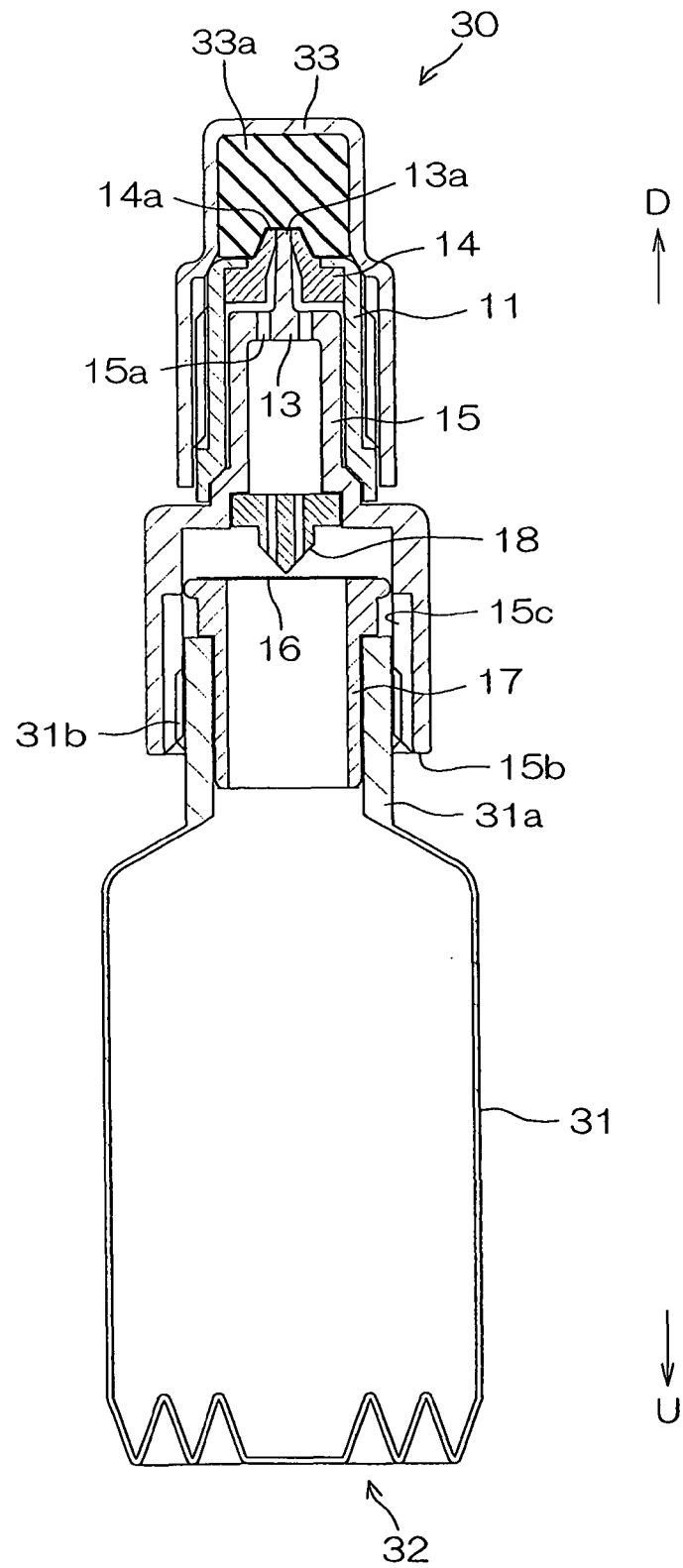
FIG. 2 is a sectional view showing an embodiment of the delivery container of the present invention.

The delivery container 30 shown in FIG. 2 is an embodiment of the delivery container of the present invention, and is provided with the delivery device 10 shown in FIG. 1 fitted at the mouth 31*a* of the squeeze bottle 31.

Figure 3A:
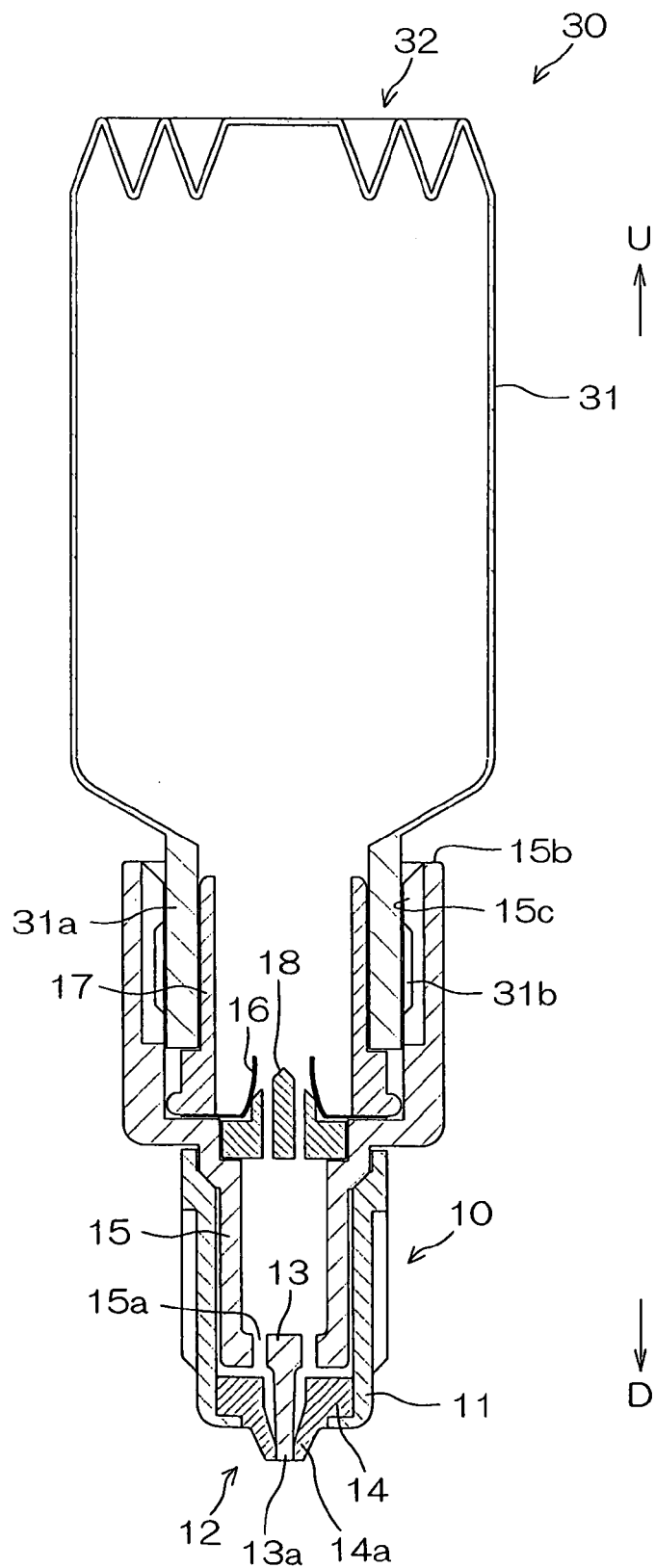
FIG. 3A through 3C are sectional views showing the delivery container shown in FIG. 2 in the state of being used.

When the delivery container 30 is not yet put in use, the threaded portion 31*b* provided on the outer circumference of the mouth 31*a* of the squeeze bottle is put in shallow screw engagement with the threaded portion 15*c* of the tube 15, and therefore the hollow needle 18 provided in the tube 15 is held in a state of not piercing a thin film 16 of a plug 17 provided at the mouth 31*a* of the squeeze bottle (FIG. 2). When the delivery container 30 is to be used, the threaded portion 31*b* of the squeeze bottle is put into deeper screw engagement with the threaded portion 15*c* of the tube, so that the thin film 16 of the plug is pierced by the hollow needle 18 (FIG. 3A). As a result, the inside of the squeeze bottle 31 and the inside of the delivery device 10 communicate with each other.

Figure 3B:
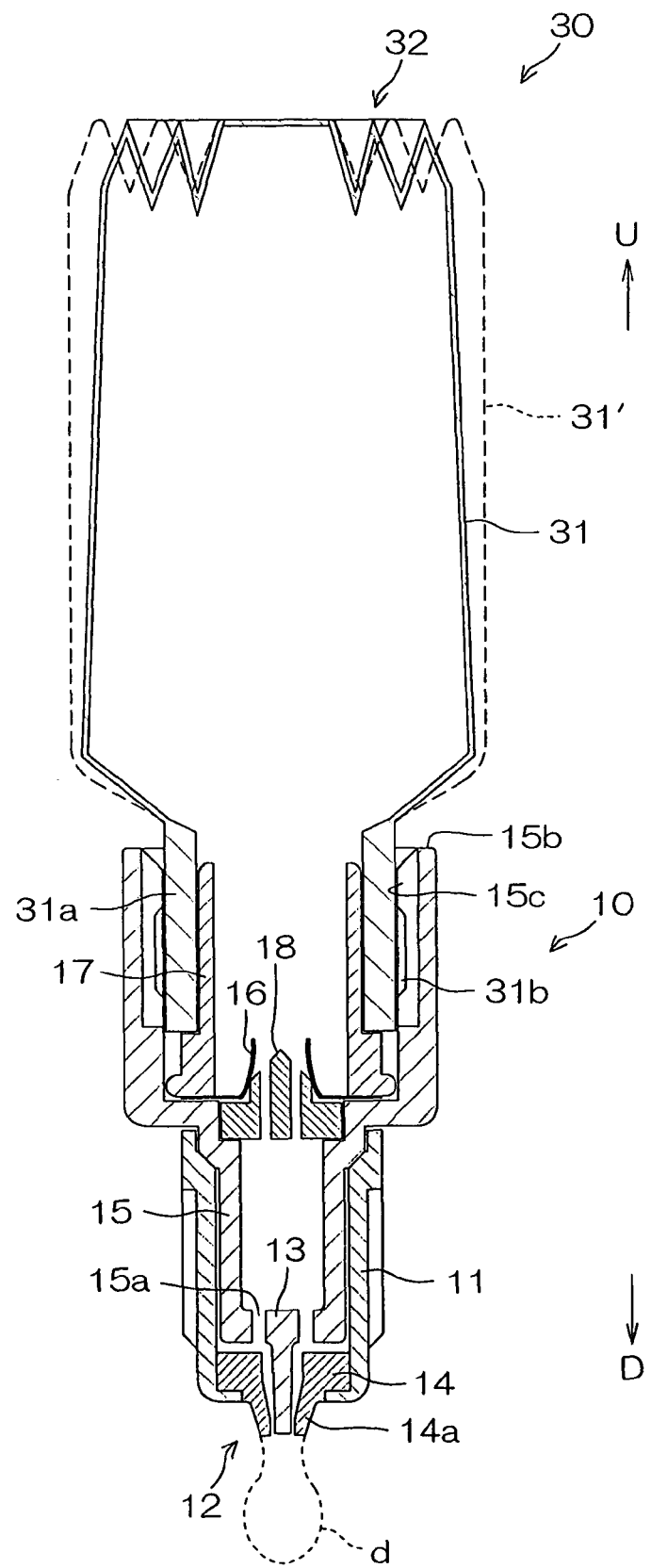

Delivery (dripping) of the content liquid from the delivery container 30 is achieved by depressing the squeeze bottle 31 (FIG. 3B). When the squeeze bottle 31 is depressed, the content liquid (not shown) contained in the squeeze bottle passes through the hollow needle 18 and the hole 13*a* of the valve element support portion 13 to reach the outlet orifice 12 in the downstream D, so as to apply liquid pressure to the distal end 14*a* of the valve element 14. The valve element 14 that has been in contact with the valve element support portion 13 to close the outlet orifice 12 deforms under the liquid pressure applied from the upstream U, so as to form a flow passage between itself and the valve element support portion 13. As a result, the content liquid passes through the flow passage and is delivered from the outlet orifice 12 in the form of drop d. When the liquid pressure applied from the upstream U is removed, the valve element 14 quickly restores the initial shape and makes contact with the valve element support portion 13, thereby closing the flow passage formed in the outlet orifice 12.

Figure 3C:
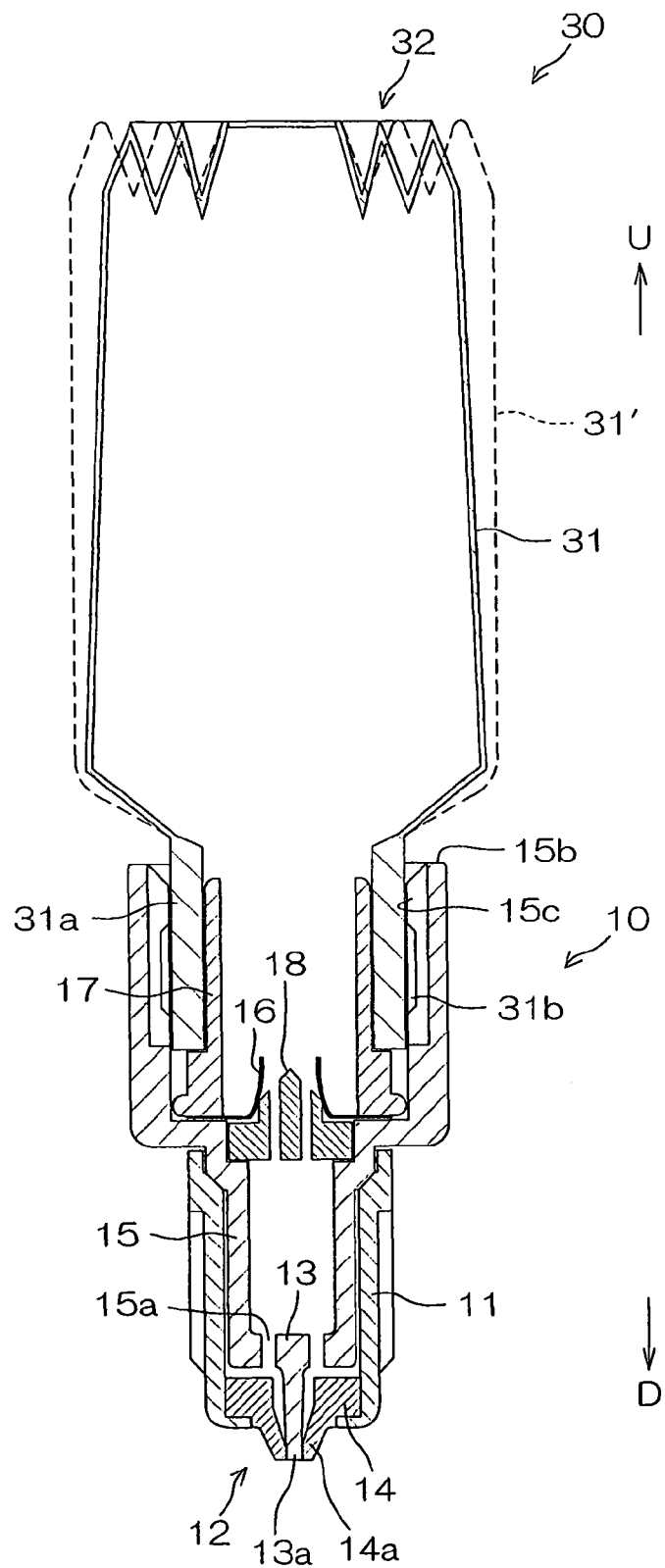

Since the squeeze bottle 31 used as the container has flexibility and a bellows portion 32 at the bottom thereof, the bottle experiences only a small force that restores the initial shape, after the bottle has been depressed to deliver the content liquid. Moreover, since the valve element 14 immediately makes contact with the valve element support portion 13 so as to close the flow passage when the liquid pressure applied from the upstream U is removed, back flow of the liquid through the outlet orifice 12 can be surely prevented and air is also prevented from entering. As a result, after the end of delivery operation is completed, the bottle 31 remains in the state of contracting the bellows portion 32, instead of restoring the shape of the bottle 31' in the state before being depressed (FIG. 3B, FIG. 3C).

Figure 4:
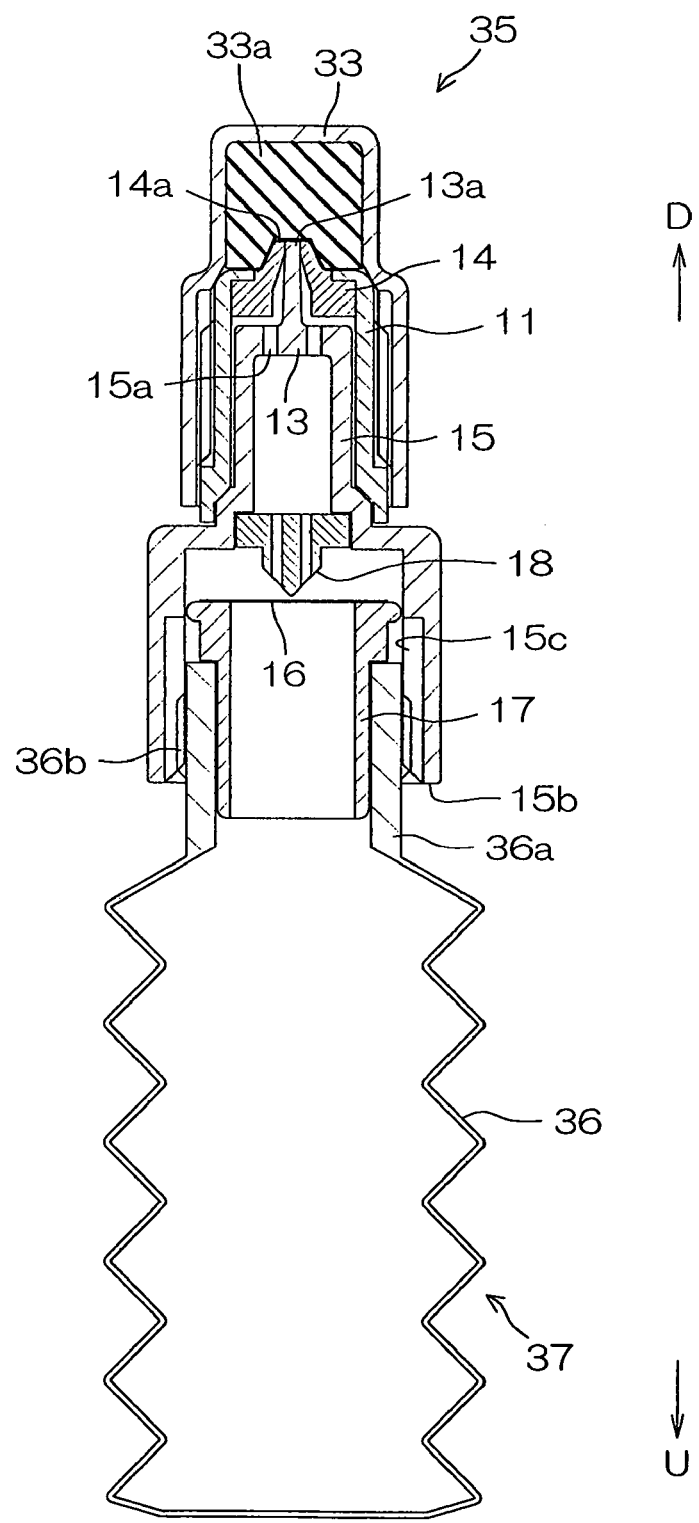
FIG. 4 is a sectional view showing another embodiment of the delivery container of the present invention.

The delivery container 35 shown in FIG. 4 is another embodiment of the delivery container of the present invention, and comprises a squeeze bottle 36 fitted with the delivery device 10 shown in FIG. 1 installed at a mouth 36a thereof.

Figure 5A:
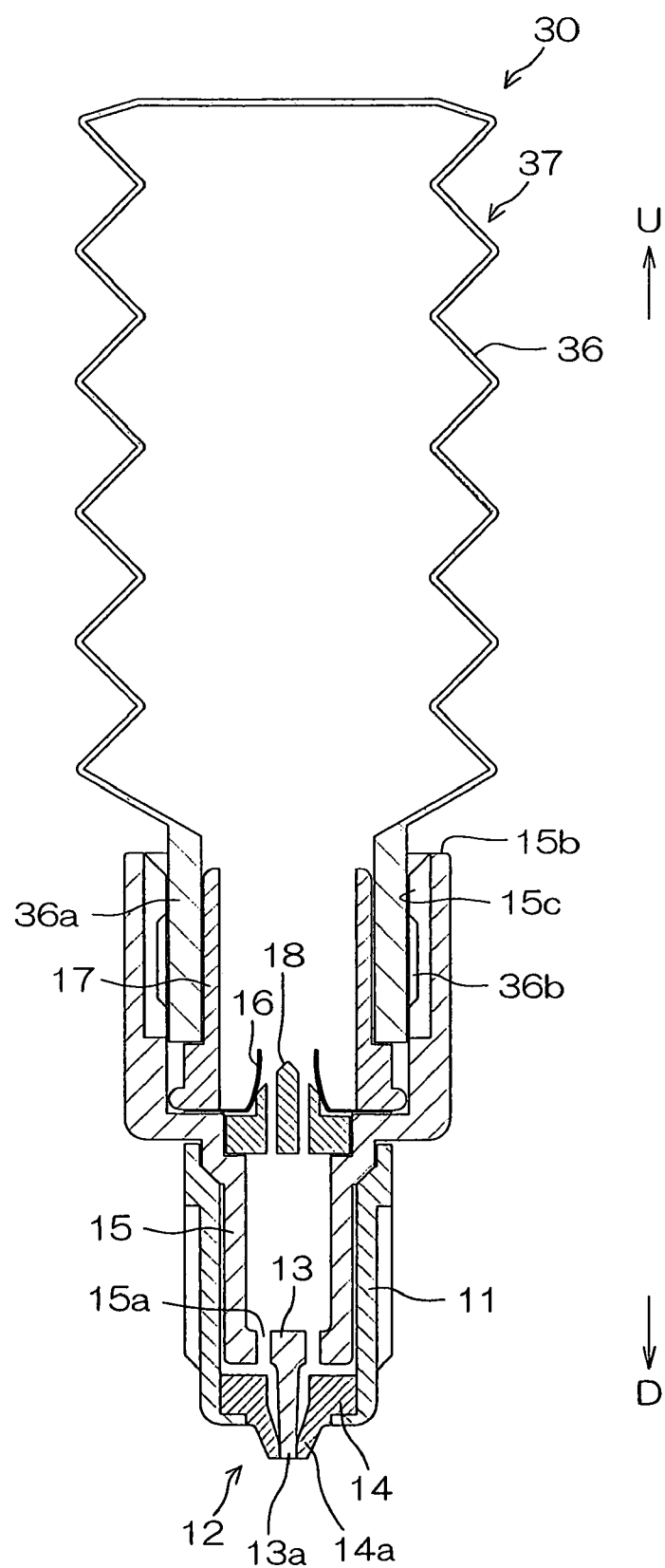
FIG. 5A through 5C are sectional views showing the delivery container shown in FIG. 4 in the state of being used.

When the delivery container 35 is not yet put in use, the threaded portion 36b provided on the outer circumference of the mouth 36a of the squeeze bottle is in shallow screw engagement with the threaded portion 15c of the tube 15, and therefore the hollow needle 18 provided in the tube 15 is held in a state of not piercing the thin film 16 of the plug 17 (FIG. 4). When the delivery container 35 is to be used, the threaded portion 36b of the squeeze bottle is put into deeper screw engagement with the threaded portion 15c of the tube similarly to the situation shown in FIGS. 3A through 3C, so that the thin film 16 is pierced by the hollow needle 18 (FIG. 5A).

Figure 5B:
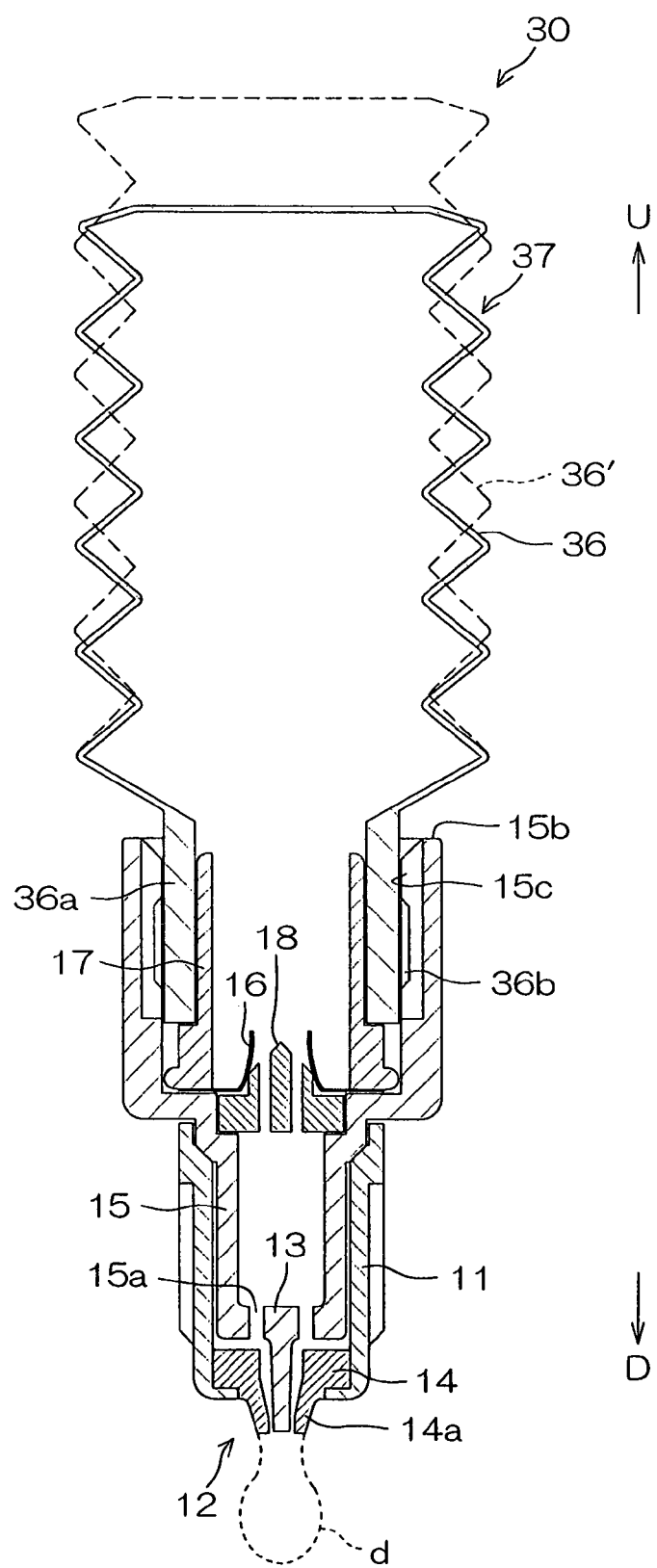
Figure 5C:
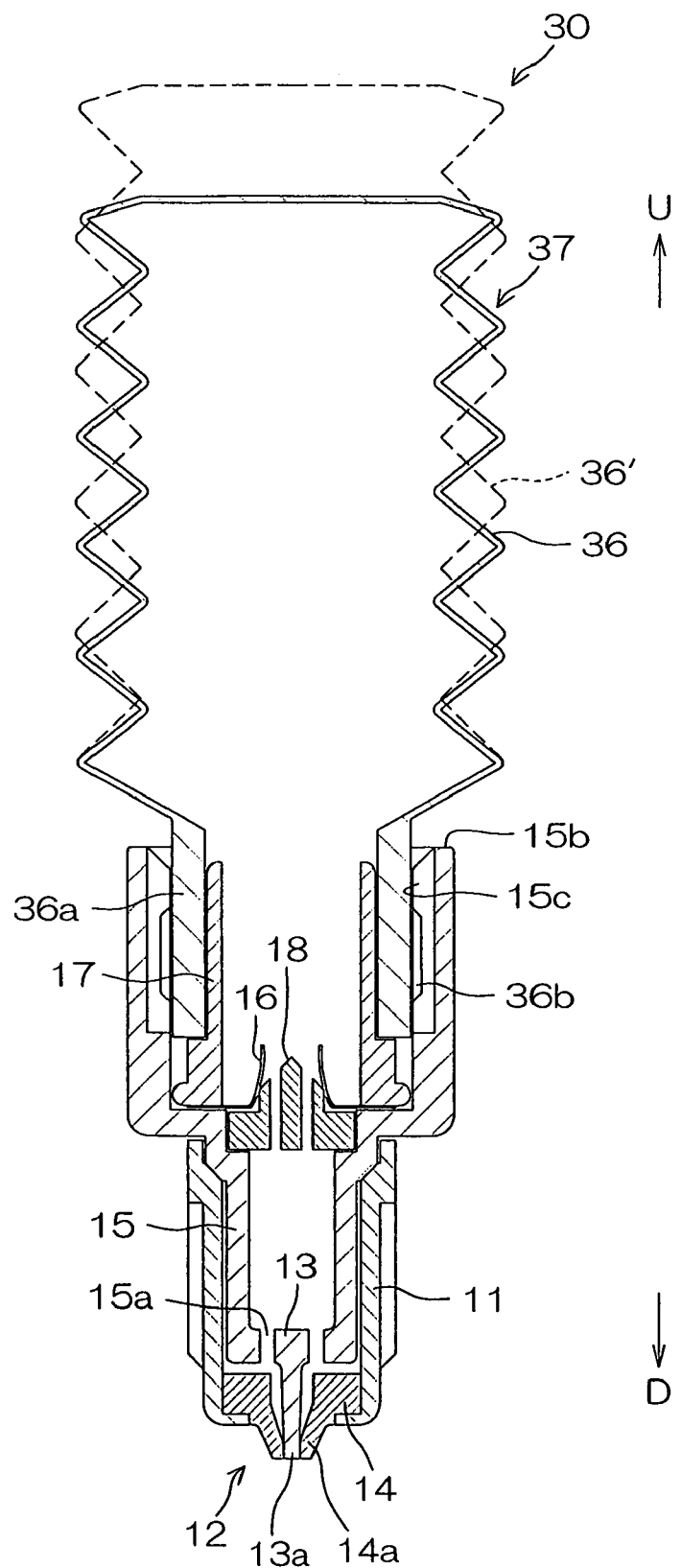

Delivery (dripping) of the content liquid from the delivery container 35 is achieved by depressing the squeeze bottle 36. When the squeeze bottle 36 is depressed, it is the same as the situation of the delivery container 30 shown in FIG. 2 and FIGS. 3A through 3C, that liquid pressure is applied to the valve element 14 so as to form the flow passage as the valve element 14 deforms, drop d is discharged through the outlet orifice 12 (FIG. 5B), the valve element 14 immediately makes contact with the valve element support portion 13 so as to close the flow passage when the pressure on the squeeze bottle 36 is removed, thereby preventing air from entering through the outlet orifice 12 into the squeeze bottle 36, while the force to restore the initial shape of the bottle 36' is small and air does not enter through the outlet orifice 12 so that the state of contracting the bellows 37 is maintained even when the pressure on the squeeze bottle 36 is removed (FIG. 5C).

Figure 6:
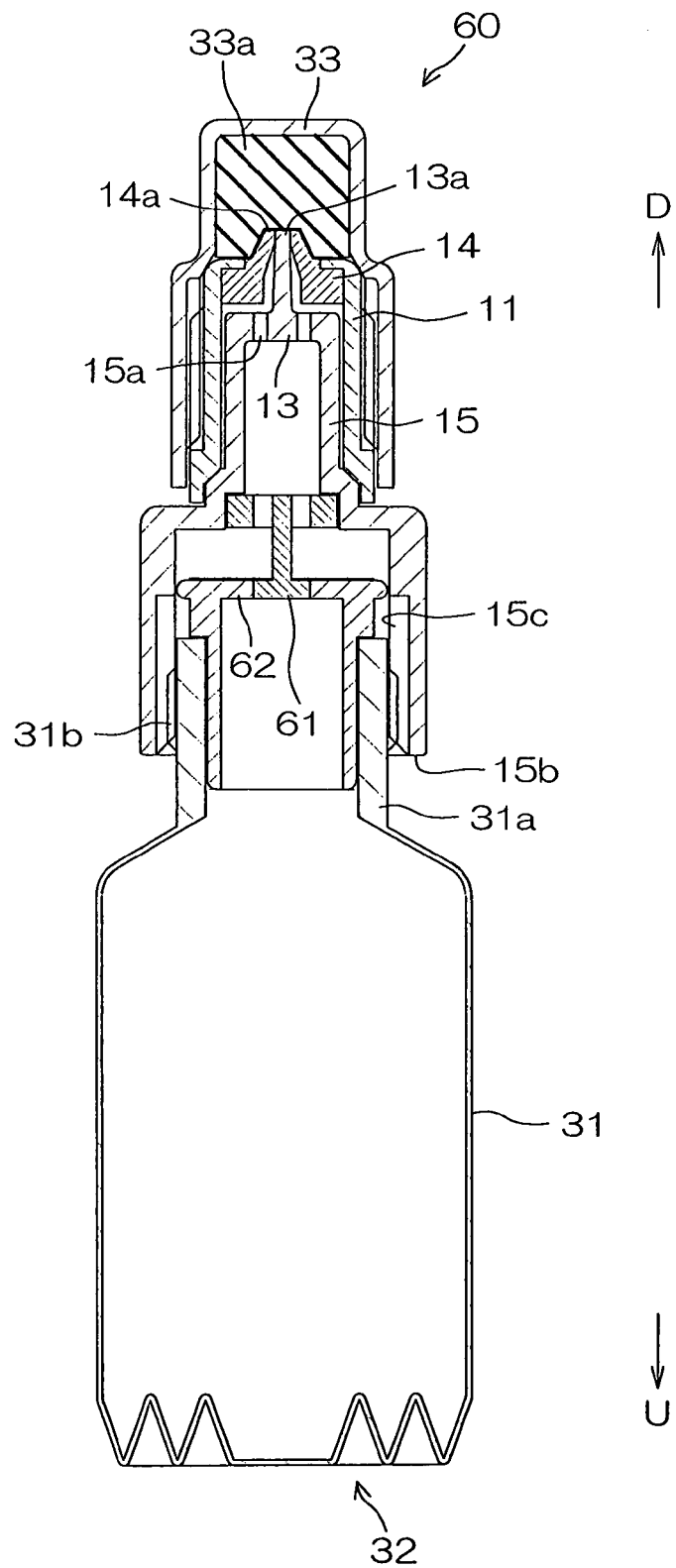
FIG. 6 is a sectional view showing further another embodiment of the delivery container of the present invention.
Figure 8:
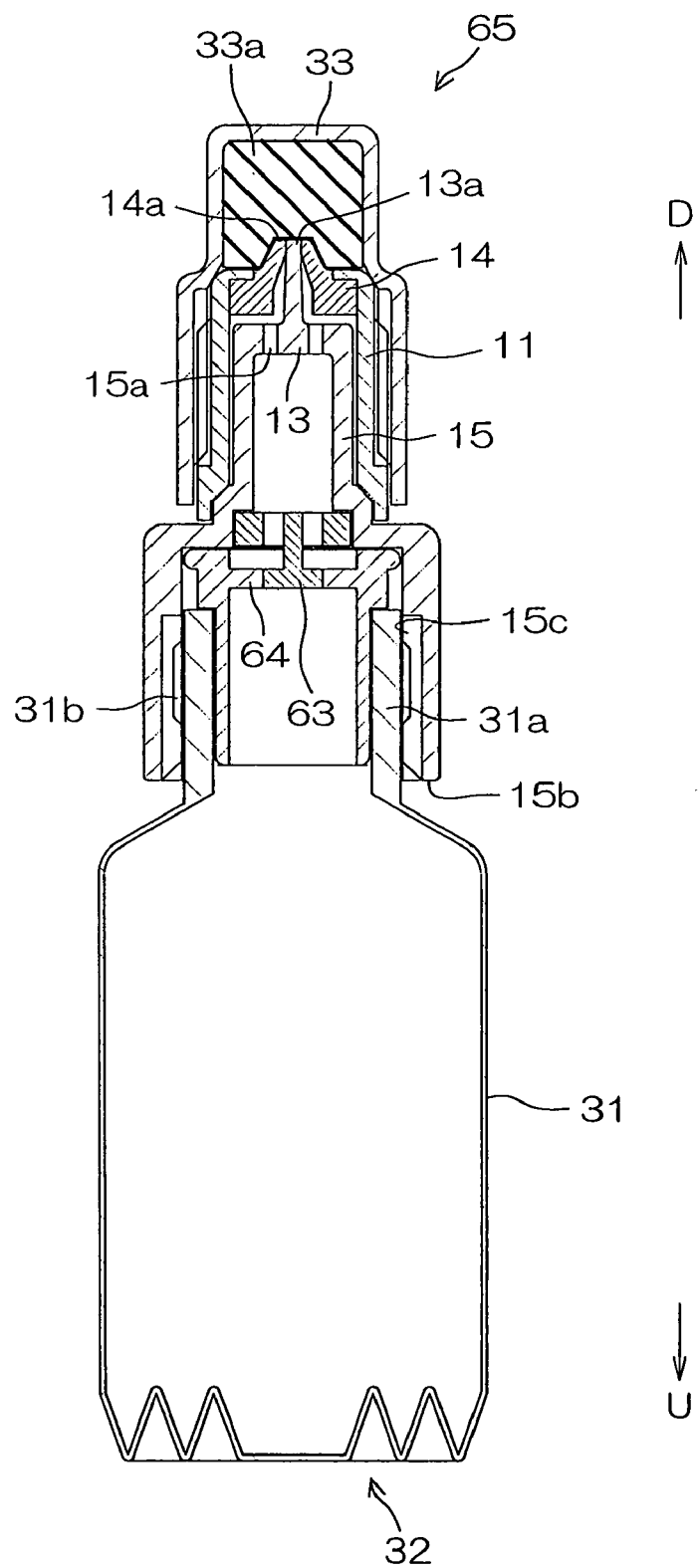
FIG. 8 is a sectional view showing further another embodiment of the delivery container of the present invention.

Delivery devices 60, 65 shown in FIG. 6 and FIG. 8 both have plugs 61, 63 instead of the hollow needle 18 in the delivery device 10, so that mouth pieces 62, 64 of the squeeze bottle 15 are opened or closed by adjusting the screw engagement between the threaded portion 15c of the tube 15 and the threaded portion 31b of the squeeze bottle 31.

Figure 7:
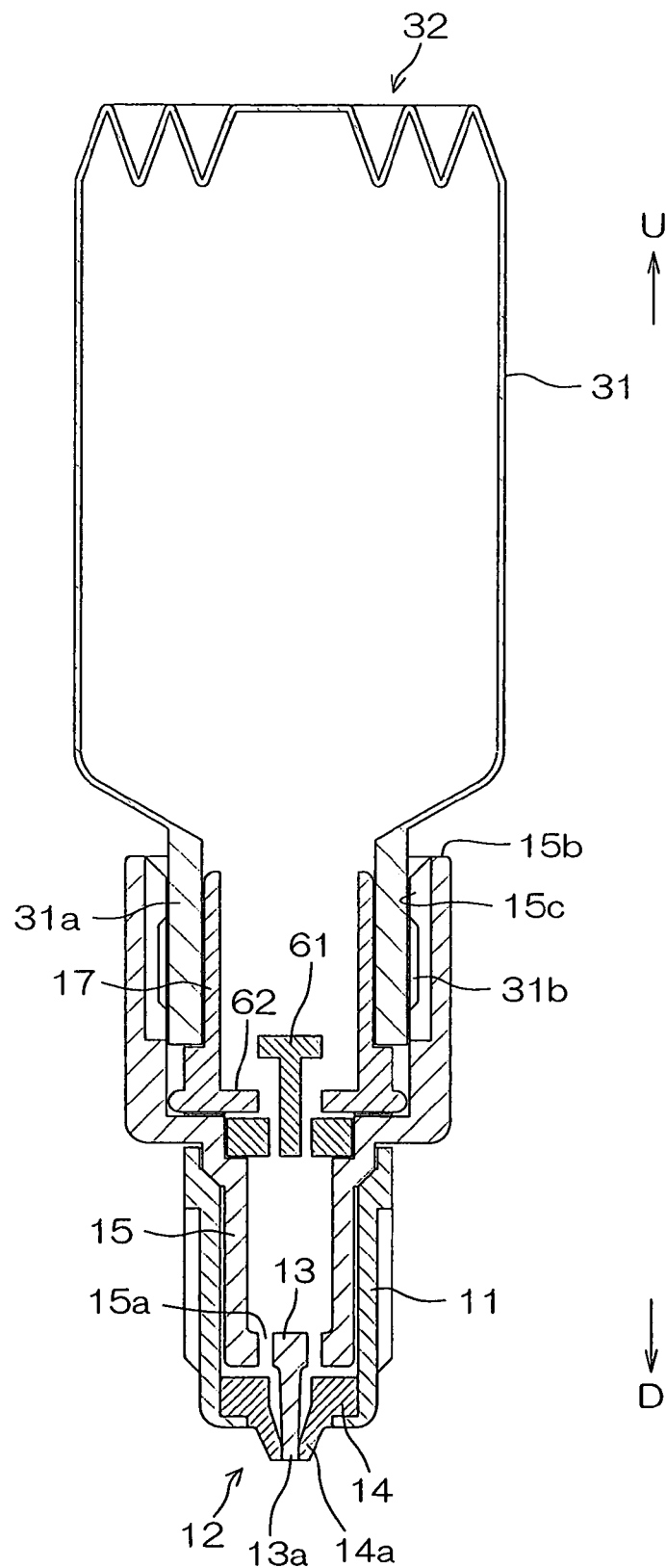
FIG. 7 is a sectional view showing the delivery container shown in FIG. 6 in the state of being used.

In the case of the delivery device 60 shown in FIG. 6, the mouth piece 62 is closed by the plug 61 when the threaded portion 15c of the tube and the threaded portion 31b of the squeeze bottle are in the state of shallow engagement with each other, and the mouth piece 62 can be opened by tightening the threaded portion 31b of the squeeze bottle and the threaded portion 15c of the tube into deeper screw engagement (FIG. 7).

Figure 9:
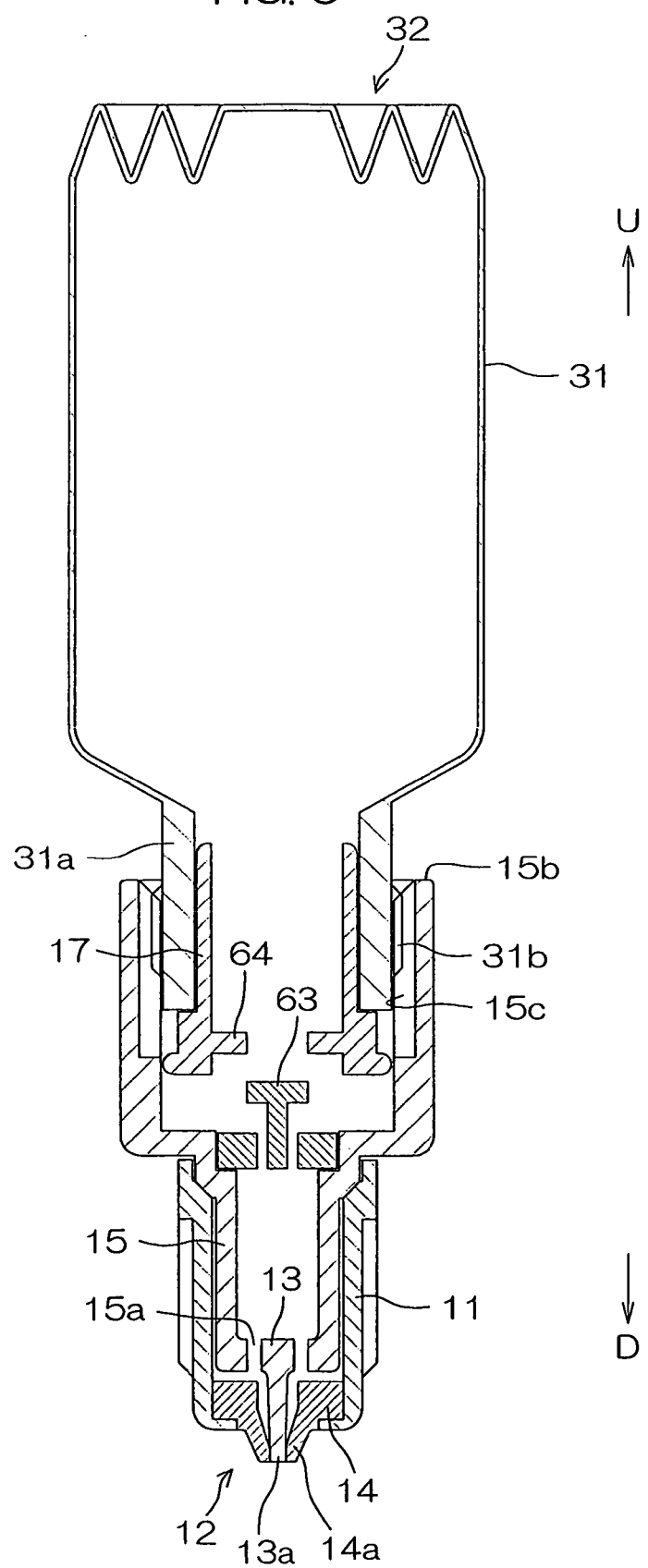
FIG. 9 is a sectional view showing the delivery container shown in FIG. 8 in the state of being used.

In the case of the delivery device 65 shown in FIG. 8, on the other hand, the mouth piece 64 is closed by the plug 63 when the threaded portion 31b of the squeeze bottle and the threaded portion 15c of the tube are in the state of deep engagement with each other, and the mouth piece 64 can be opened by loosening the relation between the threaded portion 31b of the squeeze bottle and the threaded portion 15c of the tube to make shallow screw engagement (FIG. 9).

Figure 10:
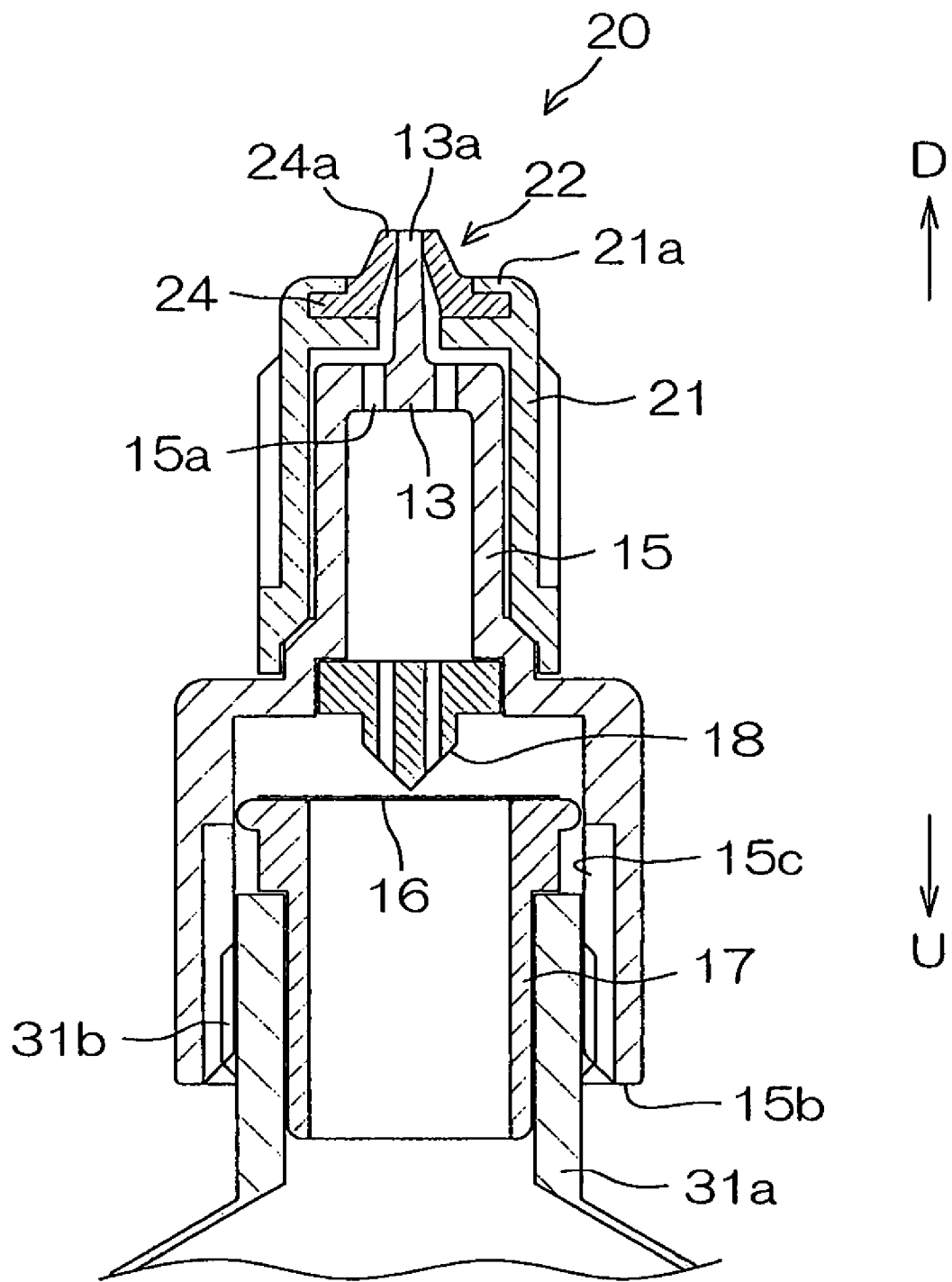
FIG. 10 is a sectional view showing another embodiment of the first delivery device of the present invention.

The delivery device 20 shown in FIG. 10 is another embodiment of the first delivery device of the present invention, and comprises an outlet portion 21 of a substantially bottomed tubular shape, a valve element support portion 13 of substantially cylindrical shape that is secured in the outlet portion 21 with the distal end 13a thereof being exposed through the outlet orifice 22 to the outside of the outlet portion 21 and a valve element 24 that is secured on the inner surface of the outlet portion 21 in the vicinity of the outlet orifice 22, with the distal end 24a thereof being exposed through the outlet orifice 22 to the outside of the outlet portion 22.

The valve element 24 of the delivery device 20 shown in FIG. 10 is not formed integrally with the outlet portion 21, but is instead molded separately and is then held by the distal end portion 21a of the outlet portion near the outlet orifice 22, so as to be secured. Since the valve element is required to undergo significant deformation under liquid pressure generated by depressing the squeeze bottle, the valve element is made of a material that has low hardness and high flexibility. As such a material is generally sticky, care must be exercised so as not to cause valve element blocking when positioning the valve element in its place in the outlet portion.

The delivery device 20 shown in FIG. 10 is similar to the delivery device 10 shown in FIG. 1 except for the difference in the configuration of the joint between the valve element 24 and the outlet portion 21.

Figure 11:
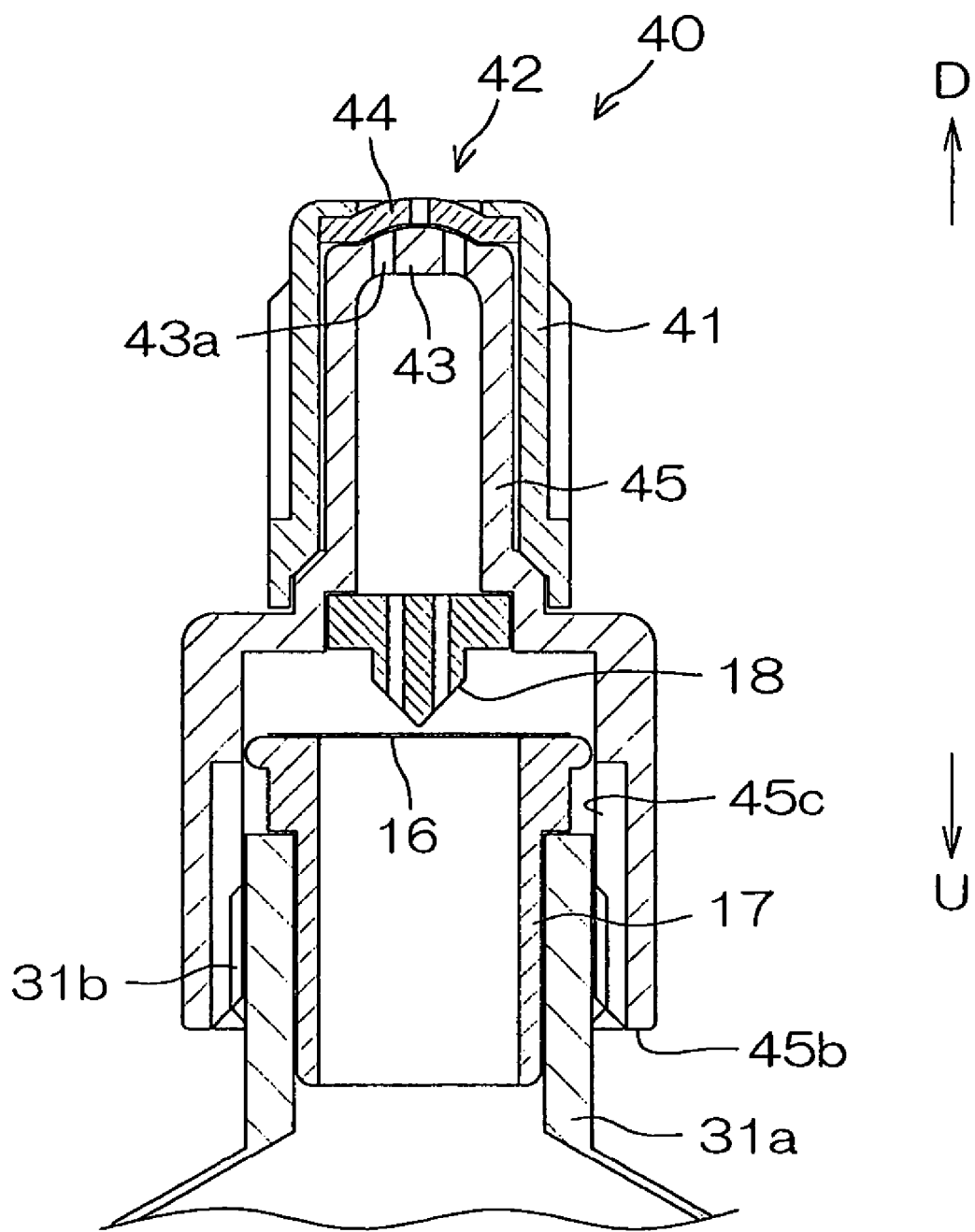
FIG. 11 is a sectional view showing an embodiment of the second delivery device of the present invention.

The delivery device 40 shown in FIG. 11 is an embodiment of the second delivery device of the present invention, and comprises an outlet portion 41 of a substantially bottomed tubular shape, a valve element support portion 43 of a substantially disk shape that is secured in the outlet portion 41 in the vicinity of the outlet orifice 42, and a valve element 44 that is secured in the outlet portion 41 with the distal end thereof exposed through the outlet orifice 42 to the outside of the outlet portion 41.

The valve element support portion 43 is connected to a tube 45, and is secured by welding the tube 45 onto the inner surface of the outlet portion 41 so that the distal end of the valve element support portion 43 having a hole 43a is positioned and secured near the outlet orifice 42. The hole 45a of the tube serves as the flow passage for the content liquid from within the tube 45 toward the outlet orifice 42. The tube 45 is put into screw engagement with the threaded portion 31b provided on the mouth 31a of the squeeze bottle 31 by screwing a threaded portion 45c provided on the inner circumference of the opening end 45b.

The valve element 44, when subjected to liquid pressure applied from the upstream U, bends toward the outside of the outlet portion 41 so as to form a flow passage between itself and the valve element support portion 43. The valve element 44 and the outlet portion 41 can be molded integrally by using a thermoplastic elastomer as the material to form the former and a thermoplastic resin as the material to form the latter. Method of molding the valve element and the outlet portion is similar to that described previously.

The delivery device 40 shown in FIG. 11 is similar to the delivery device 10 shown in FIG. 1 except for the difference in the configuration of the valve element 44 and the outlet portion 41.

Figure 12:
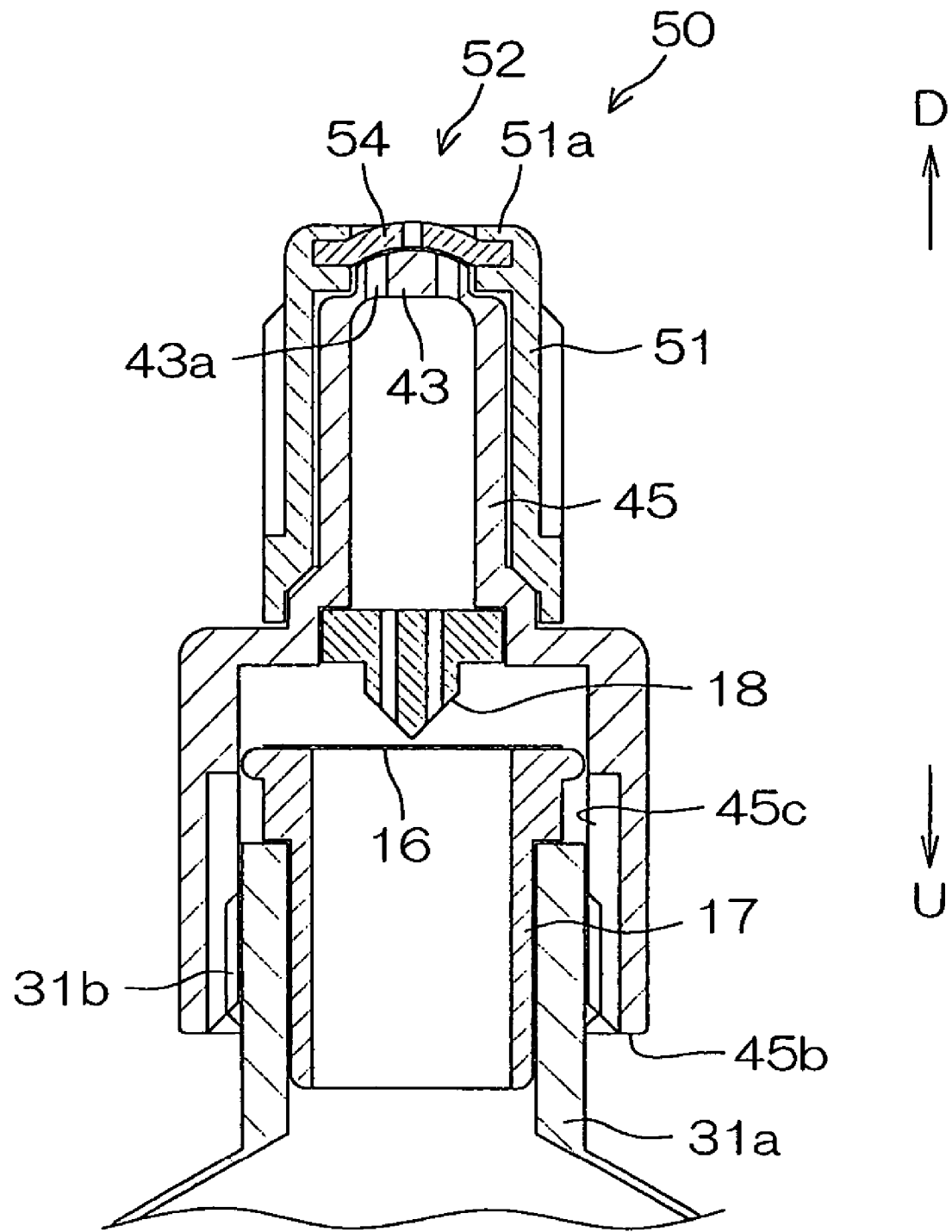
FIG. 12 is a sectional view showing another embodiment of the second delivery device of the present invention.
Figure 13A:
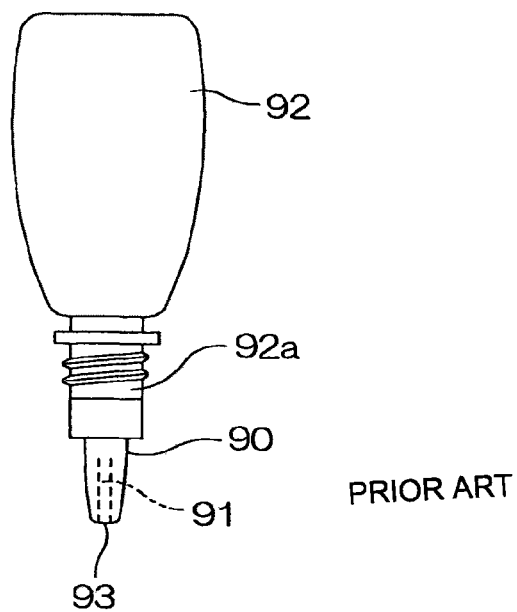
FIG. 13(*a*) is a front view showing an example of the eye dropper of the prior art, and FIG. 13(*b*) is an enlarged section view of the delivery device thereof.
Figure 13B:
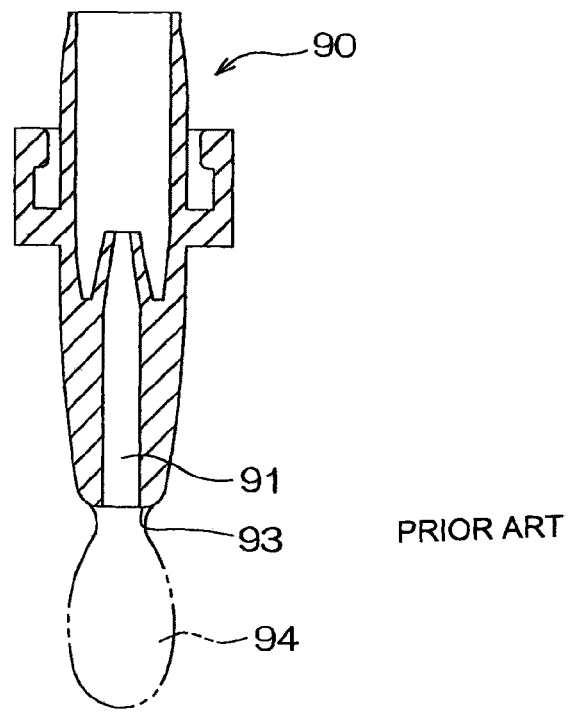
Figure 14A:
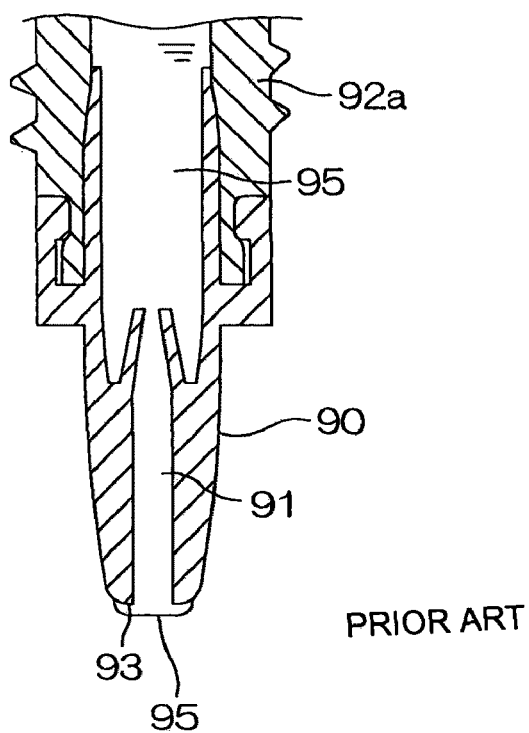
FIG. 14 is a drawing explanatory of the problems of the eye dropper of the prior art.
Figure 14B:
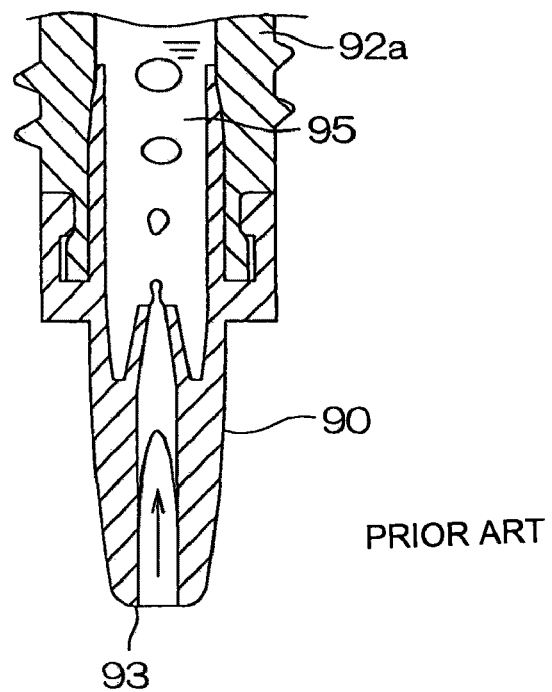

The delivery device 50 shown in FIG. 12 is another embodiment of the second delivery device of the present invention, and comprises an outlet portion 51 of a substantially bottomed tubular shape, a valve element support portion 43 of a substantially disk shape that is secured in the outlet portion 51 in the vicinity of the outlet orifice 52, and a valve element 54 that is secured in the outlet portion 51 with the distal end thereof exposed through the outlet orifice 52 to the outside of the outlet portion 51.

The valve element 54 of the delivery device 50 shown in FIG. 12 is not formed integrally with the outlet portion 51, but is instead molded separately and is then held by the distal end portion 51a of the outlet portion in a vicinity of the outlet orifice 52, so as to be secured. The delivery device 50 shown in FIG. 12 is similar to the delivery device 40 shown in FIG. 11 except for the difference in the configuration of the joint between the valve element 54 and the outlet portion 51.

The delivery devices 20, 40 and 50 shown in FIGS. 10 through 12 can also be used by attaching to the mouth of the squeeze bottle 31, 36, similarly to the delivery device 10 shown in FIG. 1.

The valve element of the delivery device according to the present invention is required to easily deform (specifically, expansion and accompanying deflection) under a liquid pressure applied from the upstream (the squeeze bottle side). As the elastic material used to form the valve element, for example, thermoplastic elastomer, natural rubber, silicone rubber, isoprene rubber, butyl rubber, butadiene rubber, fluororubber and other rubber, and gel-like material may be used.

Specific examples of the elastic material used to form the valve element are as follows. For the thermoplastic elastomer, styrene-based elastomers such as styrene-ethylene/butylene-styrene block copolymer (SEBS), styrene-butadiene-styrene block copolymer (SBS), styrene-isoprene-styrene block copolymer (SIS), modified SEBS such as modified maleic acid, styrene-ethylene/propylene-styrene block copolymer (SEPS), styrene-ethylene/butylene block copolymer (SEB) and styrene-ethylene/propylene block copolymer (SEP); olefin-based-elastomers such as ethylene-propylene copolymer; polyurethane-based elastomer and mixtures thereof may be used. Among styrene-based thermoplastic elastomers, for example, "Septon® compound" manufactured by Kuraray Plastics Co., Ltd. is preferably used. As a gel-like material, for example, gels made of linear hydrocarbon polymer (olefin-based elastomer) such as that manufactured by Cosmo Instrument Co., Ltd. under the trade name of "Cosmo Gel" and silicone-urethane-based gel such as that manufactured by Chemitech Co., Ltd. under the trade name of "Chemitech Gel" may be used. The elastic material used to form the valve element may also be a foamed material (pores are formed separately in the elastic material), with the hardness being controlled within a range to be described later by means of an additive.

While the elastic materials described above are not required to have specifically defined properties, hardness of the elastic material is preferably in a range from 0 to 40 in terms of JIS A hardness (spring hardness Hs (type A) as measured by the procedure described in JIS K 6301-5.2"Spring hardness test"), in order to achieve favorable deforming performance of the valve element. Hardness of the elastic material (JIS A) is preferably 30 or lower in the range mentioned above, more preferably 20 or lower and most preferably 10 or lower. In consideration of the material availability and strength of the valve element, the hardness may be 2 or higher.

Deforming property of the valve element under the liquid pressure is represented by, besides the hardness, modulus of compressive elasticity, for example. The elastic material used to form the valve element preferably has coefficient of permanent compressive strain CS (measured at 70° C. for 22 hours according to JIS K 7301) not higher than 50, so as not to break after repetition of loading and unloading of the liquid pressure.

In case the delivery device is used as the outlet portion of an eye dropper, pressure required to deform the valve element is preferably in a range from about 0.01 to 0.2 MPa, giving consideration to the fact that a dripping rate of an ophthalmic solution in ordinary application is about 0.05 mL/second.

When the valve element 14 or 44 is secured in vicinities of the outlet orifice of the outlet portion 11 or 41 by integral molding as in the case of the delivery device 10 or 40 shown in FIG. 1 or FIG. 11, a material having thermoplastic property may be selected from among the elastic materials described above. In case the valve element 24, 54 is held by the distal end portion 21a, 51a of the outlet portion near the outlet orifice 22, 52 as in the case of the delivery device 20, 50 shown in FIGS. 10, 12, it is not necessary to limit the elastic material used to form the valve element to thermoplastic material.

The delivery device of the present invention may be provided with a liquid control filter upstream of the outlet orifice or the valve element. The liquid control filter allows a liquid to flow therethrough only under a pressure not lower than a certain level. Providing such a filter makes it possible to prevent the liquid remaining near the outlet orifice of the outlet portion, as it may be contaminated by bacteria, dust or other contaminant, from entering the squeeze bottle. Providing the liquid control filter is preferable for preventing contaminants from entering the squeeze bottle that is connected to the delivery device.

The liquid control filter having small pores of about 0.1 to 0.45 μm across makes it difficult to apply the delivery device of the present invention to the squeeze bottle containing suspension, but is capable of preventing contaminants such as bacteria and dust from entering the squeeze bottle more reliably. The liquid control filter having relatively large pores of about 10 to 20 μm across makes it possible to apply the delivery device of the present invention to the squeeze bottle containing suspension. In this case, there is no need of taking into consideration the possible loading of the liquid control filter with the suspension. Rather, a new effect of restricting solid components of the suspension from precipitating near the outlet orifice can be achieved. Even a liquid control filter having a relatively large pore diameter has some effect of restricting the entry of bacteria, dust and other contaminants.

Liquid control filters that can be used in the present invention include, but not limited to, hydrophilic polytetrafluoroethylene (PTFE) film manufactured by Japan Gore-tex Inc., hydrophilic Durapore® made of polyvinylidene fluoride (PVDF) manufactured by Millipore Japan and hydrophilic polyether sulfone (PES) manufactured by Millipore Japan.

In the delivery device and the delivery container of the present invention, in addition to or instead of the antibacterial treatment of the outlet orifice to be described later, antibacterial treatment of a cap that covers an outer surface of the outlet portion may also be applied. Antibacterial treatment may be applied to a part of an inner surface of the cap that makes contact with the outlet orifice or an absorbing material disposed inside of the cap, but is not limited to these portions.

Since the delivery device of the present invention does not allow back flow from the outlet orifice to the upstream, residual liquid remains around the outlet orifice without entering the outlet portion after completing the liquid delivery operation. When a cap 33 having an absorbing material 33a disposed inside thereof is used, the residual liquid remaining after completing the liquid delivery operation around the outlet orifice 12 can be absorbed by the absorbing material 33a, and can be prevented from being supplied during the next delivery operation (refer to FIGS. 2, 4, 6 and 8).

The absorbing material may be designed so as to be disposed along the inner circumference of the cap instead of making direct contact with the outlet orifice, and absorb the remaining liquid that is pushed out by the inner surface of the cap.

The absorbing material may be, for example, sponge made of such a material as urethane or foamed polyethylene, cloth such as unwoven fabric, absorbent cotton or gauze, paper or hydrogel. Sponge may be formed from various known materials such as urethane and foamed polyethylene. Antibacterial treatment of sponge is preferably carried out by coating the surface of the sponge that has been formed with a medical agent such as an antibacterial agent through such means as application, or by mixing a medical agent such as an antibacterial agent in urethane or polyethylene before foaming. The absorbing material may also be made of a material that has antibacterial activity in nature.

Antibacterial treatment of cloth, paper or hydrogel may be carried out by, for example, silane coupling or selenium coating. Hydrogel may be made by mixing a polymer such as (meta) acrylamide and water-swelling clay mineral (Japanese Unexamined Patent Publication No. 2002-53629, Japanese Unexamined Patent Publication No. 2002-53762).

The outlet portion, the cap and the squeeze bottle of the delivery device and the delivery container of the present invention may be formed from a resin such as polyethylene (PE) or polypropylene (PP). PE and PP, in particular, are materials that can be safely used in pharmaceutical applications, and are preferably used in case the container of the present invention contains medical solution such as an eye dropper.

The resin used to form the outlet portion, the cap and the squeeze bottle may be mixed with an antiseptic agent or the like in advance, in order to improve the effect of preventing the residual liquid remaining around the outlet orifice after completing the liquid delivery operation and the liquid in the squeeze bottle from degenerating. As the antiseptic agent, quaternary ammonium salt (for example, "Dimer 38" and "Dimer 136" manufactured by Inui Corp.) may be used.

The outlet portion, the cap and the squeeze bottle may also be coated with the antiseptic agent on the inner surface thereof or the like through such means as application after being formed, or surface treatment such as silane coupling may be applied when forming the delivery device, the cap and the squeeze bottle. The outlet portion or the like may also be made of a resin that has antibacterial activity in nature.

It is preferable to apply antibacterial treatment to the valve element, the outlet portion (particularly the outlet orifice) and the valve element support portion of the delivery device of the present invention, but not limited thereto. When these members are subjected to antibacterial treatment, effect of preventing the reproduction of bacteria can be achieved for the liquid remaining in the vicinity of the outlet orifice after completing the liquid delivery operation.

Members subjected to antibacterial treatment may be chosen according to the constitution of the delivery device. Antibacterial treatment may be applied to various members, in addition to those described above, such as a surface of a cap that covers the outlet portion (or the outlet orifice) (the inner surface that touches the outlet portion) and the absorbing material (sponge, cloth, paper, hydrogel, etc.) disposed in the cap.

Antibacterial treatment may be carried out by mixing a chemical such as an antiseptic agent or antibacterial agent in the elastic material, such as thermoplastic elastomer that makes the valve element, or in the resin material that makes the outlet portion or the outlet orifice, or a material that forms the above-mentioned absorbing material, by coating the surface of the valve element, the outlet portion or the like that has been formed with the chemical described above, or applying surface treatment such as silane coupling or selenium coating to the material that is used to form the valve element, the outlet portion, the cap or the like. Antibacterial treatment may be applied to hydrogel that is made by mixing (meth)acrylamide-based polymer and water-swelling clay mineral by coating the surface thereof with selenium.

The present invention has been described by way of embodiments, which are intended to be mere examples and should not be interpreted as restrictive. Various modifications of the present invention that are apparent to those skilled in the art are included in the scope of the claims of patent to be described later.

INDUSTRIAL APPLICABILITY

The delivery device, the delivery container and the eye dropper according to the present invention can achieve aseptic delivery (dripping) of liquid drops while preventing the content liquid from flowing back, eliminate or reduce the use of an antiseptic agent for the purpose of preventing the content liquid from being degenerated or deteriorated, and achieve smooth delivery of the liquid without clogging even when the content liquid is a suspension, thereby providing practical utility in the field of medical container such as eye dropper containing an ophthalmic solution.

The invention claimed is:

1. An eye dropper comprising a squeeze bottle having a mouth piece at a mouth thereof, a tube having an open end installed at the mouth of the squeeze bottle and having a hole that provides a flow passage for liquid content contained in the squeeze bottle, an outlet portion of a substantially bottomed tubular shape or a substantially bowl like shape welded onto an outer surface of the tube and having an outlet orifice disposed at the bottom thereof, a valve element support portion of substantially cylindrical shape connected to a downstream end of the tube to be secured in said outlet portion and having a distal end exposed through the outlet orifice to an outside of the outlet portion, a valve element made of an elastic material that is secured in said outlet portion with a distal end thereof being exposed through the outlet orifice to the outside of the outlet portion, and a plug secured on an inner surface of the tube in the outlet portion side with respect to the open end thereof that makes contact with the mouth piece of said squeeze bottle so as to close a clearance between the outlet portion and the squeeze bottle when the tube is installed on the squeeze bottle,
wherein the distal end of the valve element makes contact with the valve element support portion so as to close the outlet orifice when there is no liquid pressure applied thereto from a side of the squeeze bottle, and deforms so as to form a flow passage between the distal end and the valve element support portion when subjected to liquid pressure applied thereto from the side of the squeeze bottle, and a flow passage is formed between the plug and the mouth piece of the squeeze bottle by screwing or fitting the tube onto the squeeze bottle, or loosening a screw engagement or fitting of the tube and the squeeze bottle.

2. An eye dropper comprising a squeeze bottle having a mouth piece at a mouth thereof, a tube having an open end installed at the mouth of the squeeze bottle and having a hole that provides a flow passage for liquid content contained in the squeeze bottle, an outlet portion of a substantially bottomed tubular shape or a substantially bowl like shape welded onto an outer surface of the tube and having an outlet orifice disposed at the bottom thereof, a valve element support portion of substantially disk shape connected to a downstream end of the tube to be secured in the outlet portion in the vicinity of the outlet orifice, a valve element made of an elastic material that is secured in the outlet portion with a distal end thereof being exposed through the outlet orifice to an outside of the outlet portion, and a plug secured on an inner surface of the tube in the outlet portion side with respect to the open end thereof that makes contact with the mouth piece of said squeeze bottle so as to close a clearance between the outlet portion and the squeeze bottle when the tube is installed on the squeeze bottle, wherein the distal end of the valve element makes contact with the valve element support portion so as to close the outlet orifice when there is no liquid pressure applied thereto from a side of the squeeze bottle, and deforms so as to form a flow passage between the distal end and the valve element support portion when subjected to liquid pressure applied from the side of the squeeze bottle, and a flow passage is formed between the plug and the mouth piece of the squeeze bottle by screwing or fitting the tube onto the squeeze bottle, or loosening a screw engagement or fitting of the tube and the squeeze bottle.

* * * * *